US007538234B2

(12) United States Patent
Iida et al.

(10) Patent No.: US 7,538,234 B2
(45) Date of Patent: May 26, 2009

(54) PREPARATION OF OPTICALLY ACTIVE 2-(1-HYDROXYETHYL)-5-HYDROXYNAPHTHO[2,3-B]FURAN-4, 9-DIONES HAVING ANTICANCER ACTIVITIES

(75) Inventors: Akira Iida, Kyoto (JP); Harukuni Tokuda, Kyoto (JP); Mitsuaki Yamashita, Takasaki (JP)

(73) Assignee: Taheebo Japan Co., Ltd., Osaka (JP)

( * ) Notice: Subject to any disclaimer, the term of this patent is extended or adjusted under 35 U.S.C. 154(b) by 2 days.

(21) Appl. No.: 12/011,759

(22) Filed: Jan. 29, 2008

(65) Prior Publication Data

US 2008/0300415 A1 Dec. 4, 2008

(30) Foreign Application Priority Data

May 31, 2007 (JP) ............................ 2007-145680

(51) Int. Cl.
*C07D 307/92* (2006.01)

(52) U.S. Cl. ...................................................... 549/458

(58) Field of Classification Search .................. 549/458
See application file for complete search history.

(56) References Cited

U.S. PATENT DOCUMENTS

| | | | |
|---|---|---|---|
| 4,739,062 | A | 4/1988 | Bigi et al. |
| 5,663,197 | A | 9/1997 | Ueda et al. |
| 6,395,773 | B1 | 5/2002 | Harai et al. |

FOREIGN PATENT DOCUMENTS

| | | |
|---|---|---|
| JP | 63-196576 | 8/1988 |
| JP | 4-139177 | 5/1992 |
| JP | 9-157196 | 6/1997 |
| JP | 9-157228 | 6/1997 |
| JP | 9-235280 | 9/1997 |
| JP | 10-130289 | 5/1998 |
| JP | 10-236986 | 9/1998 |
| JP | 11-21284 | 1/1999 |
| JP | 2004-224802 | 8/2004 |
| JP | 3598168 | 9/2004 |
| WO | WO 2004-014896 | 2/2004 |
| WO | WO 2006/098355 | 9/2006 |

OTHER PUBLICATIONS

Yamashita et al. Bioorganic and Medicinal Chemistry Letters, 17 (2007), 6417-6420, p. 6418, col. B.*

Evidence of"Exception to Lack of Novelty of Invention" submitted in Japanese patent Application No. 2007-145680 and English translation.

Fujii et al. "Ruthenium (II)-Catalyzed Asymmetric Transfer Hydrogenation of Ketones using a Formic Acid-Triethylamine Mixture". *J. Am. Chem. Soc.*, vol. 118, pp. 2521-2522 (1996).

Li et al. "An enantioselectic synthesis of phomopsolide D". *Tetrahedron Letters*, vol. 45, Issue 34, pp. 6407-6411 (2004).

Ueda et al. "Production of anti-tumor-promoting furano-naphthoquinones in *Tabebuia avellanedae* cell cultures". *Phytochemistry*, vol. 36, No. 2, pp. 323-325 (1994).

Quallich et al. "Enantioselective Oxazaborolidine Reduction of Ketones containing Heteroatoms". *Tetrahedron Letters*, vol. 34, No. 5, pp. 785-788 (1993).

Doucet et al. "*trans*-$RuCI_2$(phosphane)$_2$(1,2-diamine) and chiral *trans*-$RuCI_2$(diphosphane)$_2$(1,2-diamine): Shelf Stable Precatalysts for the Rapid, Productive, and Stereoselectric Hydrogenation of Ketones". *Angew. Chem. Int. Ed*, vol. 37, No. 12, pp. 1703-1707 (1998).

Ohkuma et al. "General Asymmetric Hydrogenation of Hetero-aromatic Ketones". *Organic Letters*, vol. 2, No. 12, pp. 1749-1751 (2000).

Yamashita et al. "Stereoselective synthesis and cytotoxicity of a cancer chemopreventative naphthoquinone from *Tabebuia avellanedae* ". *Bioorganic & Medicinal Chemistry Letters*, vol. 17, pp. 6417-6420 (2007).

Co-pending U.S. Appl. No. 11/885,216 entitled "Anticancer Compound, Intermediate Therefor, and Processes for Producing These", filed Aug. 28, 2007.

Hagiwara et al. "Domino Michael-O-alkylation reaction: one pot synthesis of 2,4-diacylhydrofuran derivatives and its application to antitumor naphthofuran synthesis", *Journal of the Chemical Society, Perkin Transaction1*, 2001, vol. 22, pp. 2946-2957.

De Oliveira et al. "Synthesis of the naturally occurring naphto-[2, 3-b]pyran-5, 10-quinones alpha caryopterone, dihydro-alpha-lapachone and 6-hydroxy-alpha-lapachone", *Tetrahedron Letters*, 1988, vol. 29, No. 2, pp. 155-158.

Chaker et al. "Studies on the oxidative additional ofN, N-Dimethylamine to bromojuglones and bromomethyljuglones". *Chem. Pharm. Bull.*, vol. 42, No. 11, pp. 2238-2240 (1994).

O'Neil (Ed) et al. *The Merck Index*. Edition Thirteen, pp. 942-943 (2001).

* cited by examiner

*Primary Examiner*—D. Margaret Seaman
*Assistant Examiner*—Nizal S Chandrakumar
(74) *Attorney, Agent, or Firm*—Hamre, Schumann, Mueller & Larson, P.C.

(57) ABSTRACT

An object of the present invention is to provide a method for efficiently preparing (S)-2-(1-hydroxyethyl)-5-hydroxynaphtho[2,3-b]-furan-4,9-dione useful as a medicine at a low cost and in large amounts. According to the present invention, the desired (S)-2-(1-hydroxyethyl)-5-hydroxynaphtho[2,3-b]furan-4,9-dione can be prepared with high efficiency at a low cost and in large amounts by asymmetrically reducing 2-acetyl-5-hydroxynaphtho[2,3-b]furan-4,9-dione in the presence of an asymmetric ruthenium complex and a hydrogen donor.

6 Claims, No Drawings

PREPARATION OF OPTICALLY ACTIVE 2-(1-HYDROXYETHYL)-5-HYDROXYNAPHTHO[2,3-B]FURAN-4,9-DIONES HAVING ANTICANCER ACTIVITIES

TECHNICAL FIELD

The present invention relates to a method for preparing an optically active 2-(1-hydroxyethyl)-5-hydroxynaphtho[2,3-b]furan-4,9-dione having anticancer activities by an asymmetric synthesis method.

BACKGROUND ART

Bignoniaceous plant *Tabebuia avellanedae* (Taheebo) is mighty tree originally come from South America, from Brazil to north Argentina. The plant is a traditional folk medicine known from the ancient Inca period, and a bark thereof has been used as a diuretic agent or an astringent. In contrast, since the plant has been focused as a medicinal resource with anticancer, antifungus, antibacterial, antiinflammatory activities and the like, researches in extraction ingredients of the plant have been developed to isolate naphthoquinones, anthraquinones, benzofuran compounds, benzene derivatives and so on. It has been known that among these isolated ingredients 2-(1-hydroxyethyl)-5-hydroxynaphtho[2,3-b]furan-4,9-dione, referred to as NQ801 hereinafter, of the formula (III):

(III)

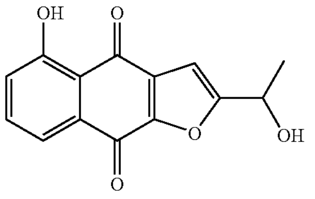

has a strong cytotoxicity as well as a potent cancer-preventing activity against various tumor cells (See, for example, Patent Document 1).

An extraction from the plant has been known as a method for obtaining NQ801. However, it is difficult to get the plant in large amounts, and further, it is very low yields of 0.05% by the extraction (See, for example, Nonpatent Document 1), and therefore, it is difficult to extract from the plant to get NQ801 in large amounts.

Additionally, a method for preparing NQ801 by organic synthesis is described in JP 2006-002482 (Patent Document 2), which has been found by the present inventors. The synthetic method comprises preparing NQ801 via an intermediate, 2-acetyl-5-hydroxynaphtho[2,3-b]furan-4,9-dione which is easily derived from 5-hydroxynaphthalene-1,4-dione (also known as juglone). In said method, NQ801 may be easily synthesized in a good yield by using as a starting material juglone which is commercially available as a chemical reagent at a relatively low cost. However, it is necessary to optically resolve the resulting NQ801, which is obtained in a racemic form, in a further step in order to get an optically active NQ801.

Patent Document 1: JP 2669762

Patent Document 2: JP 2006-002482

Nonpatent Document 1: Shinichi UEDA et al., *Phytochemistry,* 1994, Vol. 36, No. 2, p. 323-325

Nonpatent Document 2: Ryoji NOYORI et al., *J. Am. Chem. Soc.,* 1996, Vol. 118, p. 2521-2522

DISCLOSURE OF INVENTION

Problems to be Resolved by the Invention

Accordingly, it has been desired to find a method for efficiently preparing an optically active (S)-2-(1-hydroxyethyl)-5-hydroxynaphtho-[2,3-b]furan-4,9-dione useful as a medicine at a low cost and in large amounts in less steps than those of the above method.

Means of Solving the Problems

The present inventors have found that optically active NQ801 derivatives of the formula (II):

(II)

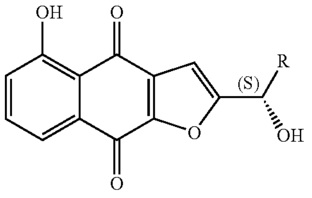

wherein R is $C_1$-$C_6$ alkyl, may be obtained in high purities and high yields by applying asymmetric reduction methods to the compound of the formula (I):

(I)

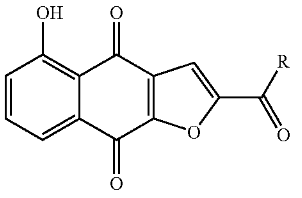

which is an intermediate in the synthetic method of the above Patent Document 2, and achieved the present invention.

That is, the present inventors have found that the compound of the formula (I) may be asymmetrically reduced in the presence of an asymmetric ruthenium complex and a hydrogen donor by using the method of Noyori et al. in Nonpatent Document 2 to prepare an optically active NQ801 in one step without generating a racemate. Additionally, the optically active NQ801 was determined an absolute configuration thereof to be confirmed as (S)-configuration by the present inventors.

The preparation of the intermediate (I) used in the present invention may be carried out according to a method disclosed in Patent Document 2 described by the present inventors. Specifically, 1,5-dihydroxynaphthalene is oxidized to synthesize 5-hydroxynaphthalene-1,4-dione (juglone). The resulting juglone is converted into 2-hydroxy juglone by amination and acid-hydrolysis, and the resultant is subjected to hydrofuran ring formation to give the intermediate ketone in a mixture thereof with the corresponding dihydro derivative (1:5). The mixture is treated with manganese dioxide to oxidize the dihydro derivative to give the ketone (I). The resulting ketone is subjected to reduction by Noyori's method described in Nonpatent Document 2 to prepare an optically active NQ801 with a high optical purity. The NQ801 thus obtained is converted into its ester with α-methoxy-α-(trifluoromethyl)phenylacetic acid (MTPA) ester, and thereby, its absolute configuration is determined to be (S)-configuration.

Effect of Invention

The present invention provides a method for efficiently preparing an optically active (S)-2-(1-hydroxyethyl)-5-hydroxynaphtho[2,3-b]-furan-4,9-dione having an anticancer activity at a low cost in large amounts. The optically active NQ801 prepared in the present invention shows almost the same cytotoxicity as mitomycin against various cancer cells.

BEST MODE FOR CARRYING OUT THE INVENTION (1) A method for preparing a compound of the formula (II):

(II)

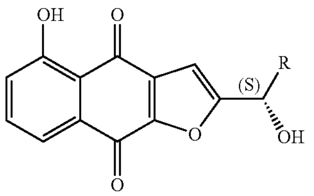

wherein R is $C_1$-$C_6$ alkyl, comprising asymmetrically reducing a compound of the formula (I):

(I)

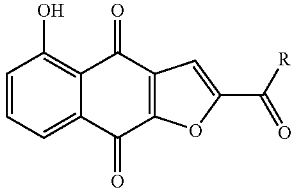

wherein R is the same as defined above, in the presence of an asymmetric ruthenium complex and a hydrogen donor.

(2) The method of (1) wherein the asymmetric ruthenium complex is selected from the group consisting of Ru[(S,S)-Tsdpen](p-cymene), RuCl[(S,S)-Tsdpen](p-cymene), RuCl [(S,S)-Tsdpen](mesitylene) and RuCl[(S,S)-Msdpen](p-cymene).

(3) The method of (2) wherein the asymmetric ruthenium complex is Ru[(S,S)-Tsdpen](p-cymene).

(4) The method of (1) wherein the hydrogen donor is a mixture of formic acid and triethylamine.

(5) The method of (4) wherein the mixture of formic acid and triethylamine is in a mixing ratio of 5:2.

(6) The method of any one of (1) to (5) wherein R is methyl.

(7) The method of any one of (1) to (6) wherein the compound may be asymmetrically reduced in a solvent at room temperature.

The term "asymmetric ruthenium complex" as used herein includes, but is not limited to, Ru[(S,S)-Tsdpen](p-cymene) (chemical name: [(1S,2S)-N-(p-toluenesulfonyl)-1,2-diphenylethanediamine]-(p-cymene) ruthenium (II)), RuCl[(S,S)-Tsdpen](p-cymene) (chemical name: chloro[(1S,2S)-N-(p-toluenesulfonyl)-1,2-diphenylethanediamine]-(p-cymene) ruthenium (II)), RuCl[(S,S)-Tsdpen](mesitylene) (chemical name: chloro[(1S,2S)-N-(p-toluenesulfonyl)-1,2-diphenylethanediamine]-(mesitylene) ruthenium (II)) and RuCl[(S,S)-Msdpen](p-cymene) (chemical name: chloro[(1S,2S)-N-(methanesulfonyl)-1,2-diphenyl-ethanediamine]-(p-cymene)ruthenium (II)), each of which is commercially-available from KANTO CHEMICAL CO., INC., preferably Ru[(S,S)-Tsdpen](p-cymene).

The term "hydrogen donor" as used herein includes alcohol, formic acid and formic acid-base mixture, but it is not limited thereto. The preferable alcohol is isopropanol. The preferable formic acid-base mixture is formic acid-triethylamine mixture. A preferable mixing ratio of the formic acid-triethylamine mixture is 5:2.

The term "$C_1$-$C_6$ alkyl" as used herein may be either of straight chain or branched chain alkyl and includes methyl, ethyl, n-propyl, iso-propyl, n-butyl, tert-butyl, n-pentyl and n-hexyl, preferably methyl.

The term "asymmetrically reducing" or "asymmetrically reduced" as used herein refers to asymmetrically reducing a ketone to an alcohol in the presence of an asymmetric ruthenium complex and a hydrogen donor.

The method for preparation of the present invention is shown to the following Scheme in combination with a step of preparing the intermediate (I) described in Patent Document 2:

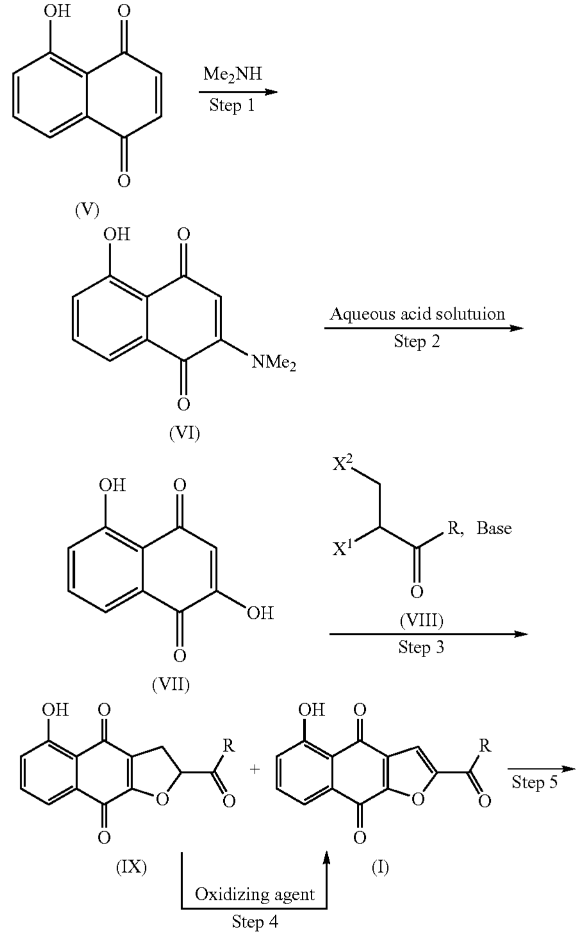

-continued

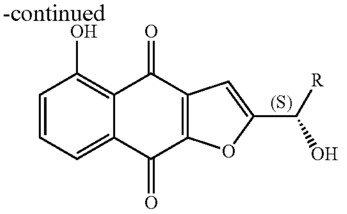

(II)

wherein R is $C_1$-$C_6$ alkyl, and each of $X^1$ and $X^2$ is independently a halogen atom. More particularly, Steps 1 to 4 in the above Scheme are described in Patent Document 2.

In Step 1 in the above Scheme, juglone of the formula (V) is reacted with dimethylamine to give a compound of the formula (VI). In addition, the starting material juglone of the formula (V) is also commercially available from, for example, TOKYO CHEMICAL INDUSTRY CO., LTD. (Tokyo, Japan).

In Step 2 in the above Scheme, the compound of the formula (VI) is hydrolyzed in an aqueous acid solution to give the compound of the formula (VII).

In Step 3 in the above Scheme, the compound of the formula (VII) is reacted with a ketone compound of the formula (VIII) in the presence of a base to give a mixture of the compound of the formula (I) and the compound of the formula (IX) (1:5).

In Step 4 in the above Scheme, a mixture of the compound (I) and the compound (IX) (1:5) obtained in the above Step 3 may be treated with an oxidizing agent to convert the compound (IX) into the compound (I).

In Step 5 in the above Scheme, the ketone of the formula (I) obtained in Step 4 is reduced in a manner as described in Noyori's Nonpatent Document 2 to prepare the optically active NQ801 with a high optical yield of 96% ee and (−)-optical rotation. The resulting NQ801 is isomerized to a diastereomer thereof by using a chiral auxiliary α-methoxy-α-(trifluoromethyl)phenylacetic acid (MTPA) to determine its absolute configuration as (S)-configuration by its chemical shift in NMR spectrum.

The reaction solvent in the method for preparation in Step 5 of the present invention includes an inert organic solvent such as dimethylformamide, dimethylsulfoxide, methylene chloride or acetonitrile, but it is not limited thereto. A preferable solvent is methylene chloride. The reaction temperature and the reaction time are usually from 0° C. to 50° C. and from 24 to 48 hours, respectively, but they are not limited thereto.

The present invention is illustrated by the following Reference Example, Example and Experiment, but it is not limited thereto.

The following apparatuses were used in the following Example. $^1$H-Nuclear magnetic resonance spectrum ($^1$H-NMR): UNITY INOVA 500 manufactured by Varian Inc., NMR measuring solvent: $CDCl_3$ (internal standard: tetramethylsilane (TMS));

Melting-point apparatus: Mp-J3 manufactured by Yanaco

REFERENCE EXAMPLE 1

Preparation of 2-acetyl-5-hydroxynaphtho[2,3-b]furan-4,9-dione

1) Preparation of 2-dimethylamino juglone (VI)

To a solution of 5-hydroxynaphthalene-1,4-dione (V) (juglone, 171 mg, 1 mmol) in toluene (5 mL) is added dimethylamine (0.75 mL, 2.0 M solution in THF, 1.5 mmol) at −40° C. The mixture is stirred at −40° C. for 1 hour, and thereto is added dimethylamine (0.75 mL, 2.0 M solution in THF, 1.5 mmol). The mixture is stirred at −40° C. for another 30 minutes, and then evaporated in vacuo. The residue is isolated to be purified by silica gel column chromatography (chloroform/ethyl acetate=20/1 (v/v)) to give 2-dimethylamino juglone (VI) (104 mg, 48%) and 3-dimethylamino juglone (20 mg, 10%).

2) Preparation of 2-hydroxy juglone (VII)

To a solution of 2-dimethylamino juglone (VI) (1.95 g, 9 mmol) in dioxane (45 mL) is added 10% hydrochloric acid (10 mL), and the mixture is heated to reflux for 30 minutes. The mixture is cooled to room temperature, and then the reaction solution is extracted with chloroform. The combined organic layer is washed with brine, dried over sodium sulfate, filtered, and evaporated in vacuo to give 2-hydroxy juglone (VII) (1.67 g, 97%) as a brownish solid.

3) Preparations of 2-acetyl-5-hydroxynaphtho[2,3-b]furan-4,9-dione (I) and 2-acetyl-2,3-dihydro-5-hydroxynaphtho[2,3-b]furan-4,9-dione (IX)

To a solution of methyl vinyl ketone (10.5 g, 150 mmol) in pentane (150 mL) is added a solution of bromine (25 g, 156 mmol) in pentane (30 mL) at −15° C. The mixture is stirred at −15° C. for 10 minutes, and then evaporated in vacuo to give a colorless oil. Then, the resulting oil is added to a solution of 2-hydroxy juglone (VII) (4.75 g, 25 mmol) in THF (250 mL). Thereto is added DBU at 0° C., and the mixture is stirred at room temperature overnight. Thereto is added 10% hydrochloric acid, and the reaction mixture is extracted with chloroform. The combined organic layer is washed with brine, dried over sodium sulfate, filtered, and evaporated in vacuo. The residue is purified by silica gel column chromatography (eluent: chloroform/ethyl acetate=9/1 (v/v)) to give an orange solid mixture (6.14 g, 95%) comprising 2-acetyl-5-hydroxynaphtho[2,3-b]furan-4,9-dione (I) and 2-acetyl-2,3-dihydro-5-hydroxynaphtho[2,3-b]furan-4,9-dione (IX) in the ratio of 1:5. The solid mixture is separated by silica gel column chromatography (eluent:chloroform) to isolate 2-acetyl-5-hydroxynaphtho[2,3-b]furan-4,9-dione (I) and 2-acetyl-2,3-dihydro-5-hydroxynaphtho[2,3-b]furan-4,9-dione (IX).

4) Preparation of 2-acetyl-5-hydroxynaphtho[2,3-b]furan-4,9-dione (I)

To a solution of 2-acetyl-2,3-dihydro-5-hydroxynaphtho[2,3-b]furan-4,9-dione (IX) (0.5 g, 1.95 mmol) in chloroform (50 mL) is added manganese dioxide manufactured by Aldrich (90% activated manganese dioxide, 10 micron, 10 g), and the resulting suspension is heated to reflux for 1 day. The suspension is cooled to room temperature, and then the mixture is filtered. The filtrate is evaporated in vacuo, and the residue is purified by silica gel column chromatography (eluent:chloroform) to give 2-acetyl-5-hydroxynaphtho[2,3-b]furan-4,9-dione (I) 0.26 g (51%).

EXAMPLE 1

Preparation of (S)-2-(1-hydroxyethyl)-5-hydroxynaphtho[2,3-b]-furan-4,9-dione

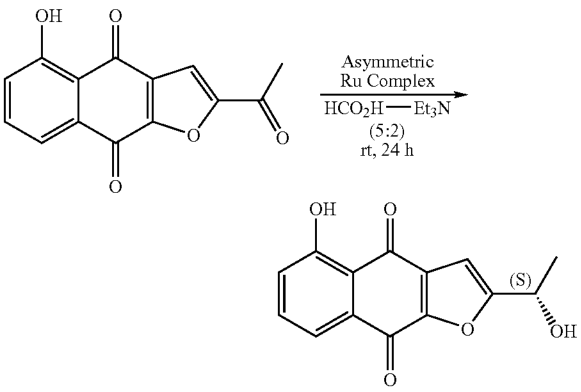

Into a flask were added 2-acetyl-5-hydroxynaphtho[2,3-b]furan-4,9-dione (128 mg, 0.5 mmol), Ru[(S,S)-Tsdpen](p-cymene) (15 mg, 0.025 mmol, 5 mol %), methylene chloride (5 mL) and formic acid-triethylamine mixture (5:2, 1.3 ml). The resulting suspension mixture was stirred at room temperature for 24 hours, and then diluted with water and 10% aqueous hydrochloric acid solution. The aqueous layer was extracted with chloroform twice, and the extract was washed with water and a saturated aqueous sodium chloride solution sequentially, and evaporated in vacuo. The residue was purified by silica gel column chromatography (eluent: hexane/ethyl acetate=2/1) to give 2-(1-hydroxyethyl)-5-hydroxynaphtho[2,3-b]furan-4,9-dione (NQ801) (115 mg, 89%, 96% ee) as a yellow crystal.

Melting Point: 171 to 172° C.

Optical Rotation: $[\alpha]^{24}_{D}$-22.7 (c0.58, $CH_3OH$)

An asymmetric yield was determined by Liquid Chromatography.

96% ee (HPLC, SUMICHIRAL, OA-4500, hexane/isopropanol/methanol=95/4/1, 1 mL/min, 254 nm, minor product: 37.9 minutes and main product: 40.9 minutes).

The resulting NQ801 with (−)-optical rotation was induced to a MTPA ester and measured $\Delta\delta(\delta_S-\delta_R)$ values to determine an absolute configuration thereof as (S)-isomer. The Δδ values obtained in the MTPA ester of NQ801 are shown as follows.

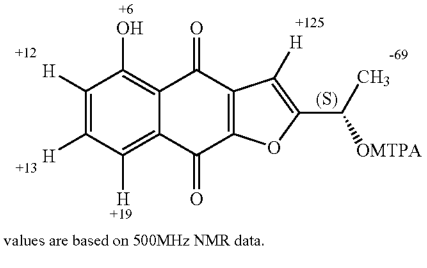

$\Delta\delta(\delta_S-\delta_R)$ values are based on 500MHz NMR data.

Experiment 1

Cytotoxicity Experiment

Cytotoxicity experiments were carried out by using human prostate cancer cell PC-3 (Invest. Urology 17: 16, (1979)), human lung cancer cell A-549 (J. Nat. Cancer Inst. 51: 1417, (1973)) and human breast cancer cell MCF-7 (cr. Table 1). Cells used in the experiments were obtained from Laboratory Products Dept. of Dainippon Pharmaceuticals Inc. (now Dainippon Sumitomo Pharma Co., Ltd.).

(1) In 3 cm plastic petri dish, $5\times10^6$ of the above human origin cancer cell was incubated at 37° C. under 5% $CO_2$ gas on an incubation medium wherein 10% fetal bovine serum (FBS) was added to a basal medium Dulbecco's modified eagle medium (DMEM).

(2) It was confirmed 1 day after the incubation that the cells were adhered to the petri dish. All incubation media were discarded, and to the cells were added fresh media (1 ml) to give reaction media. Thereto was added a solution of a test compound in DMSO (2 μl), and the mixture was incubated for 3 days under the same conditions as in the above (1).

(3) 3 days after the incubation, all cells were collected with a scrapper, and the mixture was softly stirred. Then, an aliquot (0.1 ml) was taken into a tube, and thereto was added 0.25% trypan blue solution (0.1 ml), and the mixture was stirred and then allowed to stand for 10 minutes. Both of dead and live cells suspended in the mixture were observed using a white cell counter under light microscope to calculate cytotoxicity effects to the cancer cells.

(4) The number of the observed dead cells was calculated on the basis of the total number of cells observed as 100% using a white cell counter. Each bioactivity evaluation of each compound was represented by $EC_{50}$ value (μM), which refers to a concentration of 50% of dead cells (cf. Table 1).

TABLE 1

Cytotoxicity effects of racemate NQ801, (R)-NQ801, (S)-NQ801 and Mitomycin to cancer cell lines

| | $EC_{50}$ (μM) | | |
|---|---|---|---|
| Compound | PC-3 (Prostate cancer cell) | A-549 (Lung cancer cell) | MCF-7 (Breast cancer cell) |
| Racemate NQ801 | 0.56 | 3.24 | 8.5 |
| (R)-NQ801 | 0.93 | 3 | 9.3 |
| (S)-NQ801 | 0.14 | 0.96 | 3.5 |
| Mitomycin | 0.14 | 0.43 | 0.96 |

As it is shown in the above results, (S)-NQ801 prepared by the present invention has the same cytotoxicity as mitomycin to each cancer cell.

Additionally, cancer-preventing effects about Epstein-Barr virus early antigen (EBV-EA) using Raji cell, which was available from George Klein, Karolinska Institute, Sweden, were studied (cf. Table 2).

(1) To a reaction culture (1 ml) in a 15 ml plastic tube were added $1\times10^6$ of lymphoma Raji cells of human origin, and the mixture was incubated for 2 days at 37° C. under 5% $CO_2$ gas. The reaction culture was a solution wherein butyric acid was added to RPMI-1640 (Roswell Park Memorial Institute) medium containing 8% FBS in a concentration of 4 mM. In case of positive controls, to the reaction culture was added 12-O-tetradecanoylphorbol-13-acetate (TPA) (20 ng, 32 pmol).

(2) Analysis was carried out by adding test compounds to the reaction culture in the above (1) with TPA in 1000, 500, 100 and 10 times higher concentration by mole (32, 16, 3.2 and 0.32 nmol) to TPA and incubating in a similar manner to the above.

(3) 2 days after incubation, a reaction tube was centrifuged at 1000 rpm for 10 minutes, and supernatants were discarded to collect reaction cells at the bottom of the tube, and thereto was added a phosphate buffered saline (0.1 ml) and the mixture was mixed well. To a glass slide for pathological pieces was added the mixture (5 μl), and then the mixture was air-dried to dryness.

(4) An antigen-antibody reaction was carried out at 37° C. in wet process by adding a diluted serum (1 μl) of patient with epipharynx carcinoma to the dried mixture. 45 minutes after the reaction, the resultant was washed with neutral phosphate buffer three times and then air-dried in a similar manner to the above. Then, thereto was added human blood gamma globulin antibody (1 μl), wherein a fluorescent substance was bound, to carry out an antigen-antibody reaction. 45 minutes after the reaction, the mixture was washed with neutral phosphate buffer to give a test sample.

(5) The test sample on a glass slide was observed under fluorescent light microscope. Both of dead and live cells were calculated, and the survival ratio in percentage is shown as a cancer-preventing activity, and the data of each sample were compared (cf. Table 2).

TABLE 2

Inhibitory effect of TPA-Induced EBV-EA activation

| | EBV-EA-positive cell (% survival) Compound concentration (Molar ratio/32 pmol TPA) | | | | |
|---|---|---|---|---|---|
| Compound | 1000 | 500 | 100 | 10 | $IC_{50}$ (μM) |
| Racemate NQ801 | 0 (60) | 6.2 (70) | 20.7 | 52.9 | 34.9 |
| (R)-NQ801 | 0 (70) | 9.7 | 24.7 | 59.4 | 38.9 |
| (S)-NQ801 | 0 (60) | 4.4 (60) | 16.9 | 50 | 33.2 |
| β-Lapachone | 4.7 (50) | 21.7 | 50.4 | 73.1 | 210.3 |

In Table 2, β-Lapachone means 3,4-dihydro-2,2-dimethyl-2H-naphtho(1,2-b)pyrane-5,6-dione and a known compound of the formula:

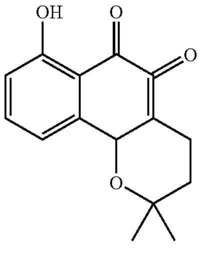

with a naphthoquinone skeleton. $IC_{50}$ represents a concentration of 50% inhibition.

It has been obvious by the above results that (S)-NQ801 prepared by the present invention inhibits EBV-EA expression.

What is claimed is:

1. A method for preparing an optically active 2-(1-hydroxyalkyl)-5-hydroxynaphtho[2,3-b]furan-4,9-dione compound of the formula (II):

(II)

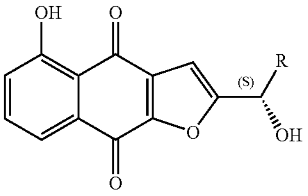

wherein R is $C_1$-$C_6$ alkyl, comprising asymmetrically reducing a compound of the formula (I):

(I)

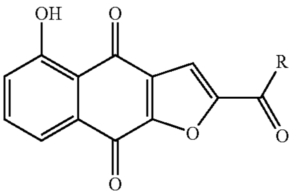

wherein R is the same as defined above, in the presence of an asymmetric ruthenium complex and a hydrogen donor, wherein the asymmetric ruthenium complex is selected from the group consisting of Ru[(S,S)-Tsdpen](p-cymene) (chemical name: [(1S,2S)-N-(p-toluenesulfonyl)-1,2-diphenylethanediamine]-(p-cymene) ruthenium (II)), RuCl[(S,S)-Tsdpen](p-cymene) (chemical name: chloro [(1S,2S)-N-(p-toluenesulfonyl)-1,2-diphenylethanediamine]-(p-cymene) ruthenium (II)), RuCl[(S,S)-Tsdpen](mesitylene) (chemical name: chloro [(1S,2S)-N-(p-toluenesulfonyl)-1,2-diphenylethanediamine]-(mesitylene) ruthenium (II)) and RuCl[(S,S)-Msdpen](p-cymene) (chemical name: chloro[(1S,2S)-N-(methanesulfonyl)-1,2-diphenylethanediamine]-(p-cymene) ruthenium (II)).

2. The method according to claim 1, wherein the asymmetric ruthenium complex is Ru[(S,S)-Tsdpen](p-cymene).

3. The method according to claim 1, wherein the hydrogen donor is a mixture of formic acid and triethylamine.

4. The method according to claim 3, wherein the mixture of formic acid and triethylamine is in a mixing ratio of 5:2.

5. The method according to claim 1, wherein R is methyl.

6. The method according to claim 1, wherein the compound may be asymmetrically reduced in a solvent at room temperature.

* * * * *

UNITED STATES PATENT AND TRADEMARK OFFICE

CERTIFICATE OF CORRECTION

PATENT NO. : 7,538,234 B2
APPLICATION NO. : 12/011759
DATED : May 26, 2009
INVENTOR(S) : Iida et al.

It is certified that error appears in the above-identified patent and that said Letters Patent is hereby corrected as shown below:

Column 8, line 8: "cr. Table 1" should read --cf. Table 1--.
Column 9, lines 45-55, the formula should be replaced with the formula shown below:

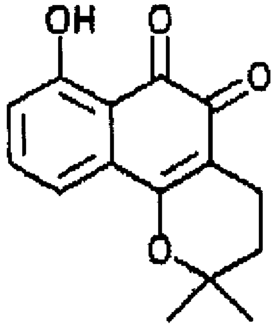

Signed and Sealed this

Twenty-ninth Day of December, 2009

David J. Kappos
*Director of the United States Patent and Trademark Office*